April 27, 1943. A. KREBS Plant Pat. 577

ROSE

Filed June 2, 1941

INVENTOR
Alfred Krebs
By Lyon & Lyon
Attorneys

Patented Apr. 27, 1943

Plant Pat. 577

UNITED STATES PATENT OFFICE

577

ROSE

Alfred Krebs, Montebello, Calif., assignor to Edward E. Marsh, Pasadena, Calif., and himself, jointly Application June 2, 1941, Serial No. 396,316

1 Claim. (Cl. 47—61)

This invention relates to a new and distinctive variety of rose which may be generally designated as a red rose of the Cecil Brunner type.

The parentage of the rose bush is not exactly known but was produced through cross-pollenization of several varieties or classes of roses, among which were the common variety of Cecil Brunner rose, and a rose bush produced by cross-pollenization and which is similar to the "World's Fair," but whose parentage is not now known, and is an unnamed rose. The particular rose illustrated is a second generation cross-pollenization of one of the rose bushes resulting from the aforesaid cross-pollenization and further cross-pollenized with the common variety of Cecil Brunner rose.

The new and distinct variety of rose embracing this invention is characterized by the following distinct characteristics:

1. *Color.*—Generally designated as red and specifically hereinafter described.

2. The shape and size of the bud, which closely follows, or is allied to, the shape and size of the common Cecil Brunner rose, but which is characterized by particularly long lapels which encompass the bud prior to opening and extend in length beyond the bud and are of a very fine barbed structure as illustrated.

3. The more dainty formation of the leaf structure and the fine barbed outline of each of the leaves and wherein the leaves are more abundantly associated with the bud structure than is true of the ordinary Cecil Brunner rose.

4. The color of the leaves at the bud—which are a reddish green.

5. A characteristic found it is believed only in this particular rose and as illustrated in the accompanying figures wherein the bud on opening is a deep shaded crimson red, maintaining substantially this color as it opens during the second day, and then during its third day of development shading down in depth of color to a rose crimson of lighter color density, followed with an apparent change back to substantially its bud color and density of color as the rose opens to its fully opened condition.

6. The bush has no thorns.

7. The bush or rose of the bush is characterized further in that it develops its full scent when in full bloom and its scent as the bud opens is very delicate and the scent increases in intensity to where its full scent or fragrance is found in the full bloom.

8. It is further characterized in being a very vigorous grower, more so even than the ordinary variety of Cecil Brunner.

9. It is further characterized in that the buds, even though closed when cut, will open in water without showing loss in color density and even though the bud be completely closed when placed in the water to the extent that no rose color is showing, which makes the bush particularly valuable for propagation for use in floral establishments for decorative purposes and for use in the preparation of corsages or the like.

10. The rose of the bush is further characterizer in its long-lasting qualities. The rose on the bush develops on the average during a period of five days from the opening of the bud to its stage of full bloom. During this development the bud develops to where, on the fourth day, it has reached the bloom condition illustrated in Figure 1 from the opening bud as illustrated in Figure 2. The rose reaches its full bloom on the fifth day. The rose in full bloom is illustrated by the fully opened rose in Figure 2.

11. It is further characterized in its lasting qualities in that the closed bud in water required about three days to open as a bud with the sepals separated from the petals as shown by the bud of Figure 2; also in the long period of development as hereinabove described and in the fact that the bush is subject to forced hothouse cultivation without appreciable loss in color density.

12. The rose and the bush are further characterized in being extremely mildew and pest-resistant.

As illustrated in Figure 2, below the fully developed rose is a bud with the sepals separated from the petals, as during the first day of development.

Specifically illustrating the color formation of the bud, open rose and leaf structure as the same are compared with the color plates of the Horticultural Colour Chart issued by The British Colour Council in collaboration wth The Royal Horticultural Society, volume I:

The color of the bud during the first day's development compares with, but is not identical to, the crimson color of Plate 22 in the lighter shade of crimson there illustrated, and shades into a deeper crimson as illustrated, for which there is no comparable color plate.

The leaf structure of the leaves or sepals of the bud compares with Plate 58/1 designated as "Paris Green," the color of the leaves being shaded to more dense green from the green of the sepal shade of Paris Green as described.

During the second day of development, the rose color near the tip of the petals compares favorably with Plate 21/1 entitled a light-shade of "Carmine," while the color of the petals near the base thereof is comparable with color Plate 22, entitled "Crimson." The lapels or sepals have a color which compares favorably with Plate 59, entitled "Cyprus Green," while the leaf color has remained substantially as in the first day's development.

In the third day's development the color at the base of the bud has remained comparable with that of Plate 21/1 entitled "Carmine," while the lighter shade indicated near the edge of the petals is comparable with Plate 21/2 (a lighter shade of Carmine). The leaf structure has remained substantially constant in color.

Figure 1:
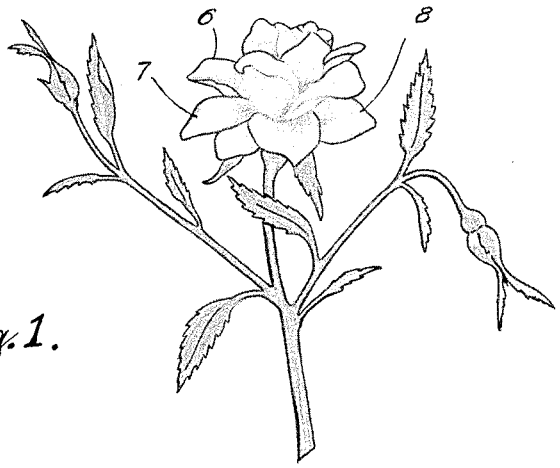
Figure 1 is of the fourth day development of th bud to where it has progressed to opening.

On the fourth day's development as illustrated in Figure 1, the color at the petal portion 6 is comparable with the same color Plate 21/1, that is, of one of the lighter shades of Carmine, while the petal structure of the rose deepens through the shades indicated at 7 and 8 progressively by comparison with Plate 21, "Carmine" to Plate 22, "Crimson."

Figure 2:
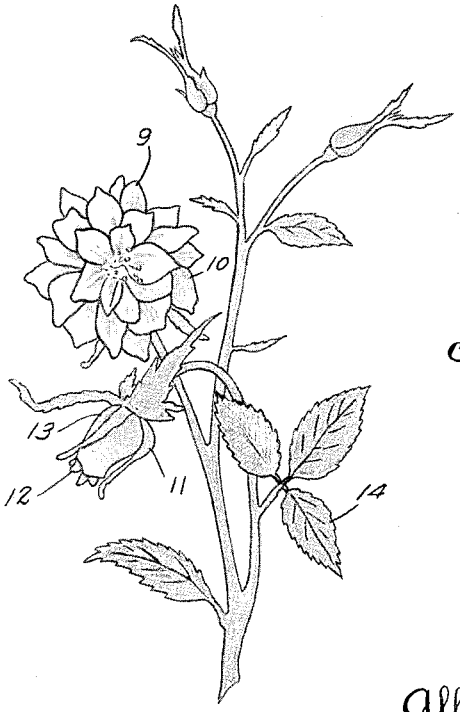
Figure 2 illustrates the fifth day condition of development of the bud to full bloom, which condition the full bloom of the rose will retain for approximately three days before the petals of the rose drop.

On the fifth day's development as illustrated in Figure 2, the fully opened rose color at the petal portions marked 9 compares with Plate 621, "Carmine Rose," deepening in color to the portion indicated at 10, which compares with the Plate 21/1 "Carmine." The new opening bud indicated at 11, which has opened in water, has the color characteristic at the portion indicated at 12, comparable with Plate 623, designated "Neyron Rose" and deepens in color to the portion indicated at 13, which is comparable again with color Plate 21/1 "Carmine." The leaf color at this stage of development is such that the characteristic color of the leaf 14 is comparable with Plate 57/1, i. e., "Nickel Green" at its lightest portion, deepening to, but not exactly like, the Plate 56 entitled "Chrysocollagreen."

I claim:

The bush rose herein described characterized by its crimson-carmine shaded buds, retaining the same color to open bloom, characterized in the long, barbed sepals of the bud structure, characterized in the dainty multiple barb formation of the leaves, the lack of thorns, its vigorous growing qualities, its long-lasting qualities, the ability of the buds to open in water when cut, and in that the full scent of the rose develops in full bloom, and further characterized in that the size and shape of the bud and rose very closely approximate that of the common variety of Cecil Brunner.

ALFRED KREBS.